(12) United States Patent
Fischer

(10) Patent No.: US 9,833,661 B2
(45) Date of Patent: Dec. 5, 2017

(54) STATIONARY EXERCISE EQUIPMENT FOR PHYSICAL TRAINING, MORE PARTICULARLY AN EXERCISE BIKE

(75) Inventor: Andreas Fischer, Nuremberg (DE)

(73) Assignee: PROTOKON GYARTO, FEJLESZTO ES KERESKEDO KFT., Kiskoros (HU)

( * ) Notice: Subject to any disclaimer, the term of this patent is extended or adjusted under 35 U.S.C. 154(b) by 189 days.

(21) Appl. No.: 13/587,446

(22) Filed: Aug. 16, 2012

(65) Prior Publication Data
US 2013/0085038 A1    Apr. 4, 2013

(30) Foreign Application Priority Data

Sep. 29, 2011   (DE) .................. 10 2011 114 521

(51) Int. Cl.
*A63B 15/02*    (2006.01)
*A63B 24/00*    (2006.01)
(Continued)

(52) U.S. Cl.
CPC .......... *A63B 24/0087* (2013.01); *A63B 22/00* (2013.01); *A63B 24/0062* (2013.01);
(Continued)

(58) Field of Classification Search
CPC ..... G06F 1/1649; G06F 1/1454; A63B 24/00; A63B 23/0476; A63B 21/005;
(Continued)

(56) References Cited

U.S. PATENT DOCUMENTS 3,735,101 A    5/1973  Stewart
4,616,823 A *  10/1986 Yang .............................. 482/57
(Continued)

FOREIGN PATENT DOCUMENTS

DE    197 44 219 A1    4/1999
DE    201 13 786 U1    1/2002
(Continued)

OTHER PUBLICATIONS

European Search Report issued in counterpart European Application No. EP 12174380.1 dated Jan. 24, 2013.
(Continued)

*Primary Examiner* — Nyca T Nguyen
(74) *Attorney, Agent, or Firm* — Lucas & Mercanti, LLP

(57) ABSTRACT

Stationary exercise equipment for physical training, more particularly an exercise bike, comprising a frame with a movement unit which either is to be moved by the exerciser or is itself driven and interacts with the exerciser, one or more sensors, assigned to the movement unit and/or the exerciser, for capturing measured values, and a computer apparatus for establishing one or more items of measurement-value-related information, which are output on a frame-side display apparatus, letterized in that provision is made for a first display apparatus, which is directed at the exerciser for displaying one or more items of information, and in that provision is made for a second display apparatus, which is directed at the opposite side for outputting at least one item of information.

11 Claims, 3 Drawing Sheets

(51) Int. Cl.
*A63B 71/00* (2006.01)
*A63B 22/00* (2006.01)
*A63B 71/06* (2006.01)
*A61B 5/00* (2006.01)
*A61B 5/024* (2006.01)

(52) U.S. Cl.
CPC ...... *A63B 24/0075* (2013.01); *A63B 71/0619* (2013.01); *A63B 71/0697* (2013.01); *A61B 5/0002* (2013.01); *A61B 5/02438* (2013.01); *A63B 2024/0065* (2013.01); *A63B 2024/0081* (2013.01); *A63B 2071/0658* (2013.01); *A63B 2220/803* (2013.01); *A63B 2220/833* (2013.01); *A63B 2220/836* (2013.01); *A63B 2230/06* (2013.01)

(58) Field of Classification Search
CPC . A63B 69/16; A63B 22/06; A63B 2024/0081; A63B 24/0087; A63B 24/0062; A63B 71/0619; A63B 71/0697; A63B 71/0658; A63B 21/28; A63B 21/285; A63B 24/0075; A63B 24/0081; A63B 2024/0065; A63B 2024/0068; A63B 2024/0071
USPC ............... 482/2, 3, 4, 5, 6, 7, 8, 9, 57, 1, 54
See application file for complete search history.

(56) References Cited

U.S. PATENT DOCUMENTS

| | | | |
|---|---|---|---|
| 4,919,416 A | | 4/1990 | DeCloux |
| 5,171,196 A * | | 12/1992 | Lynch ................................ 482/7 |
| 5,207,623 A * | | 5/1993 | Tkatchouk ........ A61M 16/0045 482/61 |
| 5,524,637 A * | | 6/1996 | Erickson ........................ 600/592 |
| 5,769,755 A * | | 6/1998 | Henry et al. ...................... 482/8 |
| 7,465,257 B1 * | | 12/2008 | Morgan, Jr. ..................... 482/57 |
| 7,981,000 B2 * | | 7/2011 | Watterson et al. ............... 482/8 |
| 2002/0055419 A1 * | | 5/2002 | Hinnebusch ...................... 482/8 |
| 2003/0134714 A1 * | | 7/2003 | Oishi ..................... A63B 24/00 482/6 |
| 2005/0239601 A1 * | | 10/2005 | Thomas ........................... 482/1 |
| 2006/0247098 A1 * | | 11/2006 | Raniere ............................ 482/8 |
| 2008/0015088 A1 * | | 1/2008 | Del Monaco ..................... 482/4 |
| 2008/0165080 A1 * | | 7/2008 | Reddy et al. .................. 345/1.1 |
| 2009/0270227 A1 * | | 10/2009 | Ashby et al. ..................... 482/8 |
| 2009/0286655 A1 * | | 11/2009 | Parks et al. ...................... 482/9 |
| 2010/0156625 A1 * | | 6/2010 | Ruha ........................ 340/539.12 |
| 2011/0172060 A1 * | | 7/2011 | Morales et al. .................. 482/8 |
| 2011/0183813 A1 * | | 7/2011 | Barker et al. ..................... 482/8 |

FOREIGN PATENT DOCUMENTS

| | | |
|---|---|---|
| EP | 0 174 747 A2 | 3/1986 |
| EP | 1 878 473 A1 | 1/2008 |
| WO | 2007000774 A2 | 1/2007 |

OTHER PUBLICATIONS

Office action dated Sep. 14, 2015 for European Application No. 12174380.1-1658.

* cited by examiner

STATIONARY EXERCISE EQUIPMENT FOR PHYSICAL TRAINING, MORE PARTICULARLY AN EXERCISE BIKE

CROSS-REFERENCE TO RELATED APPLICATION

This application claims the priority of DE 10 2011 11.4 521.8 filed Sep. 29, 2011, which is incorporated by reference herein.

BACKGROUND OF THE INVENTION

The invention relates to stationary exercise equipment for physical training, more particularly an exercise bike, comprising a frame with a movement unit which either is to be moved by the exerciser or is itself driven and interacts with the exerciser, one or more sensors, assigned to the movement unit and/or the exerciser, for capturing measured values, and a computer unit for establishing one or more items of measurement-value-related information, which are output on a frame-side display apparatus.

In recent years in particular, the notion of fitness is undergoing a significant change from a more strength-oriented training to a health-oriented training. To this end, use is often made of stationary exercise equipment, which, in particular, serves for endurance training. The most prominent example of such stationary exercise equipment is an exercise bike, having a frame, a saddle on which the exerciser sits and corresponding handles and pedals by means of which a flywheel mass or the like is moved. However, treadmills on which the exerciser runs, which are driven and the speed and incline of which can be varied, should also be mentioned in this context.

Within the scope of the health-oriented training, various measured values are recorded using one or more suitable sensors, said measured values being tapped firstly on the exercise equipment itself and secondly also on the exerciser himself. While, for example, in the case of the equipment, the cadence or rotational speed is measured by a suitable rotational-speed sensor or a reed contact, the power in watts is measured by suitable strain gauges, a sensor system or other suitable measurement methods and a specific resistance level is measured by setting a corresponding gear ratio, an incline and the like by means of a measurement sensor system, it is usually the heart rate that is captured as a person-related measured value, for example by means of a pulse watch or chest strap worn by the exerciser.

A specific heart rate zone in which the heart rate should lie in order to achieve a specific training goal can be established from, in particular, the person-related measured values, i.e. predominantly the heart rate, in conjunction with additional data to be entered by the user, i.e. to be stored in a computer apparatus. The user data to be entered (e.g. sex, age, weight, training activity, etc.) are used to calculate a maximum heart rate on the basis of which specific training zones, which encompass frequency ranges, can thereupon be established and these are used for training control. It is conventional for five main training zones to be defined, which define specific training goals. These are defined in percentage ranges with respect to the maximum personal heart rate and range from a health zone in the region of 50-60% of the maximum heart rate through a fat-burning zone (60-70%), an aerobic zone (70-80%) and an anaerobic zone (80-90%) up to a "red zone", i.e. a warning zone, which reaches between 90-100% of the maximum heart rate. Depending on the desired training goal, the exerciser can now set his activity such that his measured actual heart rate is within the desired training zone.

In the case of so-called stand-alone equipment, the heart rate is captured and displayed by means of an individual system, for example by using a pulse watch which is worn by the exerciser. This serves firstly for capturing the other data to be entered and secondly also for capturing the actual heart rate and also serves as a display apparatus on which the exerciser can read off the information. The remaining training data (rotational speed, power, etc.) are captured on the equipment side and are reproduced on a separate display apparatus.

In the case of group fitness in particular, which is becoming ever more attractive, a trainer or instructor who runs the training and, because different people train together, has to provide individual training instructions finds that individual support is virtually impossible because he has no access to or overview over the personal measured values and hence the data.

As a result of this, it is known practice within the field of so-called group or multi-user solutions to send the information, i.e. the measured heart rate, captured by the person-related measurement equipment, e.g. the chest strap, to a central reception station which is connected to a computer apparatus and a display apparatus. This also captures the personal data of the individual members of the group, to which are accordingly assigned the measured heart rates, from which the appropriate training zones, etc. are then established and displayed. Thus, the display is in this case no longer provided individually, but rather centrally on a screen from which the training leader notes the measured values of all his participants. In this case although the trainer sees the individual loads and training zones of the group members there is no individual display of the training data at the place of the exerciser himself. Moreover, the trainer loses all control and the overview if he leaves his place to provide assistance to one exerciser or another. Secondly, the individual exerciser is unable to identify his own load profile because the training-zone-related information is not displayed to him, only the equipment-related information such as cadence, etc.

BRIEF SUMMARY OF THE INVENTION

Here, the invention is based on the problem of specifying stationary exercise equipment, which enables improved training control by an improved information display.

In order to solve this problem in the case of stationary exercise equipment of the type mentioned at the outset, provision according to the invention is made for providing a first display apparatus, which is directed at the exerciser for displaying one or more items of information, and for providing a second display apparatus, which is directed at the opposite side for outputting at least one item of information.

According to the invention, two separate display apparatuses are provided on the exercise equipment, said display apparatuses being aligned toward two different sides, consequently enabling the displayed information to be noted by different persons. The first display apparatus is directed at the exerciser; all relevant data can be displayed thereon, provided that it is determined by the equipment-related computer apparatus. On the one hand, this is all of the training data captured on the equipment side (cadence/rotational speed, power, resistance, etc.) and also the person-related data such as, in particular, the heart rate and the maximum heart rate or a possible derived training zone etc., depending on what person-related information is established. That is to say that in this respect there is also communication between the sensors, which capture the person-related data, and the equipment-side computer apparatus. This of course only applies to the extent that this data is captured, which may naturally be different depending on the exercise equipment. This is because parallel capture of the equipment-related and person-related measured values is not mandatory; depending on the type of equipment, it is also possible for only the one or the other set of measured values to be captured and processed or displayed.

According to the invention, provision is furthermore made for a second display apparatus which is directed at the opposite side, consequently in the direction of the trainer. At least one item of information which is relevant to the trainer and decisive for possible person-related training commands is displayed on this display apparatus. Of course, this information displayed thereon is predominantly person-related information, i.e., for example, the heart rate or information derived therefrom, more particularly the training zone in which the exerciser currently is in. Establishing a training zone, for example, is alternatively also possible by using the current wattage, captured on the equipment side, and the FTP index (the maximum power which a rider can provide in an hour in the case of aerobic/anaerobic metabolism; this should be entered manually), i.e. establishing and displaying training zones can be implemented not only by using the heart rate. In general, the information relating to the training zone is a decisive item of information for the trainer, which he requires for optimizing the training. In each case, this information is also displayed for the trainer directly on the exercise equipment, and so he obtains this central item of information even if he is moving throughout the room. Within the scope of group fitness, it is conventional for the exercise equipment to be arranged e.g. in a semicircle or in offset rows such that the trainer, when standing in front of the group, can see all exercise equipment from the front. As a result, he can also see all display apparatuses which are arranged on the front side of the equipment facing him, and so he can immediately have an overview of the corresponding information when he approaches the respective equipment.

That is to say that in the case of the exercise equipment according to the invention, the relevant information in particular (including in particular specifically the heart-rate-related information), which is relevant to both the exerciser and the trainer, is displayed to both the exerciser and the trainer.

Here, the displayed information base provided for the exerciser can be substantially broader because, depending on the extent being captured, all equipment-related information (cadence, resistance, etc.) and also his person-related information can be displayed to him. By contrast, it is sufficient for the trainer to obtain a performance indicator, which specifically reflects the personal load on the participant, i.e. in particular the heart-rate-related information, provided this is captured. Equally, information in respect of the cadence or the power etc. can naturally also (alternatively or additionally) be displayed to the trainer, from which the trainer, optionally without knowledge of the heart rate or training zone, can derive information in respect of the performance on the basis of his experience in order to be able to intervene in order to provide assistance.

However, what is decisive in any case here is the display of information on two sides on one piece of exercise equipment, which allows both the exerciser and the trainer to note the information.

In the process, it is particularly advantageous if the information which can be output on the second display apparatus can simultaneously be displayed with identical information which can be output on the first display apparatus. By way of example, only one item of information can be displayed on the second display apparatus, which is directed towards the trainer. In terms of information content, this item of information is the same as an item of information displayed on the first display apparatus directed towards the exerciser; this means that the exerciser and the trainer obtain the same information and consequently have the same level of information in respect of a decisive item of information, wherein the form of the display can be the same or different. In any case, the simultaneous display is important so that both have the same level of information at all times.

It is self-evident that it is also possible to display a number of identical items of information simultaneously on the first and the second display apparatus, i.e., for example, a first heart-rate-related item of information (e.g. training zone) and a second equipment-related one (e.g. cadence). Ultimately, this depends on what information is specifically established and on the type of utilized display apparatuses.

For the first display apparatus, which is directed at the exerciser, use is preferably made of a display, more particularly a color display. Such displays can be installed in very different sizes; they offer a sufficiently large information area for displaying a multiplicity of items of information. Moreover, if designed as a touchscreen, it also enables direct data entry. Alternatively, the information can also be provided for the exerciser by one or more color LEDs or other conspicuous color indicators.

The second display apparatus, i.e. the display apparatus facing the trainer, can also be a display, more particularly a color display. It too can be variable in terms of its size, and so it is also possible to display thereon a sufficient breadth of information or, if only one item of information is displayed, to display the latter in a sufficiently large fashion such that the trainer can immediately note it, even from a certain distance. As an alternative to the use of a display, more particularly a color display, it is also possible to install a plurality of light sources, more particularly LEDs, which shine in different colors. As a result of the different colors, these light sources can represent corresponding color-coded information, wherein it is possible, for example, to associate the different colors with different training zones.

If color displays are respectively used for the first and second display apparatus, the same information, which is displayed on both displays, is preferably represented in an identical color display in each case. In particular, if this item of information is the training zone, the latter can easily be displayed in a color-coded fashion. However, a color-coded display is also possible in the same manner if the same information is displayed on a color display as a first display apparatus and a corresponding colored light source as second display apparatus.

As such a color display on a color display, the display background in particular is displayed in color. Independently of whether both display apparatuses are embodied as color displays, or whether only the first display apparatus is a color display, the information can be visually represented by complete coloring of the display background, i.e. the basic color. Naturally, further text information, symbols or the like can also be displayed on this colored background area, particularly on the first display apparatus if additional information such as the cadence etc. are to be displayed.

Identical information can also be displayed on both displays by letters, text or symbols, independently of whether said displays are normal black/white displays or color displays. By way of example, a specific training zone can also be displayed by an appropriate letter, for example by the letters A-E in the case of five training zones, or by possible other symbols. Naturally, a cumulative display of identical information is also possible, wherein a first item of identical information is displayed by the same color coding and a second item of information is displayed by the same symbols, letters or numerals.

Moreover, an item of information can for example also be displayed by a flashing display, particularly if the first display apparatus is a color display and the second display apparatus comprises a plurality of light sources, more particularly LEDs. In this case, information can be displayed by a flashing display on the color display (in doing so, the whole background can flash, or only a specific display section on the display), and blinking of the light source (on/off) can be displayed. Ultimately, the flashing can encode further information, for example warning information provided to the exerciser and the trainer, for example if a training zone is changed, in order to draw the attention of both addressed persons immediately to the change. That is to say, firstly, the color marks the corresponding training zone, and flashing operation displays the change of zone.

The first display apparatus is to be attached to the exercise equipment in a known manner; by way of example, in the case of an exercise bike it is found in the region of the handlebar. The second display apparatus is arranged on a suitable vertical or horizontal brace of the frame, for example by means of a suitable holder or by integration, i.e. fixed insertion into this brace. By way of example, if a display is provided, the latter is for example fixedly installed into a corresponding recess in the brace; the same applies to optional LEDs or the like, and so it is possible to route the corresponding feed lines in the interior of the hollow brace to the equipment-side, central computer apparatus, at which all measured values captured by the arbitrary sensors converge.

As an alternative to this, it is possible to arrange the first display apparatus, the second display apparatus and the computer apparatus on or in a common housing, which is preferably attached to the handlebar. It follows that all relevant components are connected to form a compact unit that is easy to handle as a result of the integration on or in a common housing.

BRIEF DESCRIPTION OF THE DRAWINGS

Further advantages, features and details of the invention emerge from the exemplary embodiments described in the following text, and from the drawing, in which.

DETAILED DESCRIPTION OF THE PREFERRED EMBODIMENTS

Figure 1:
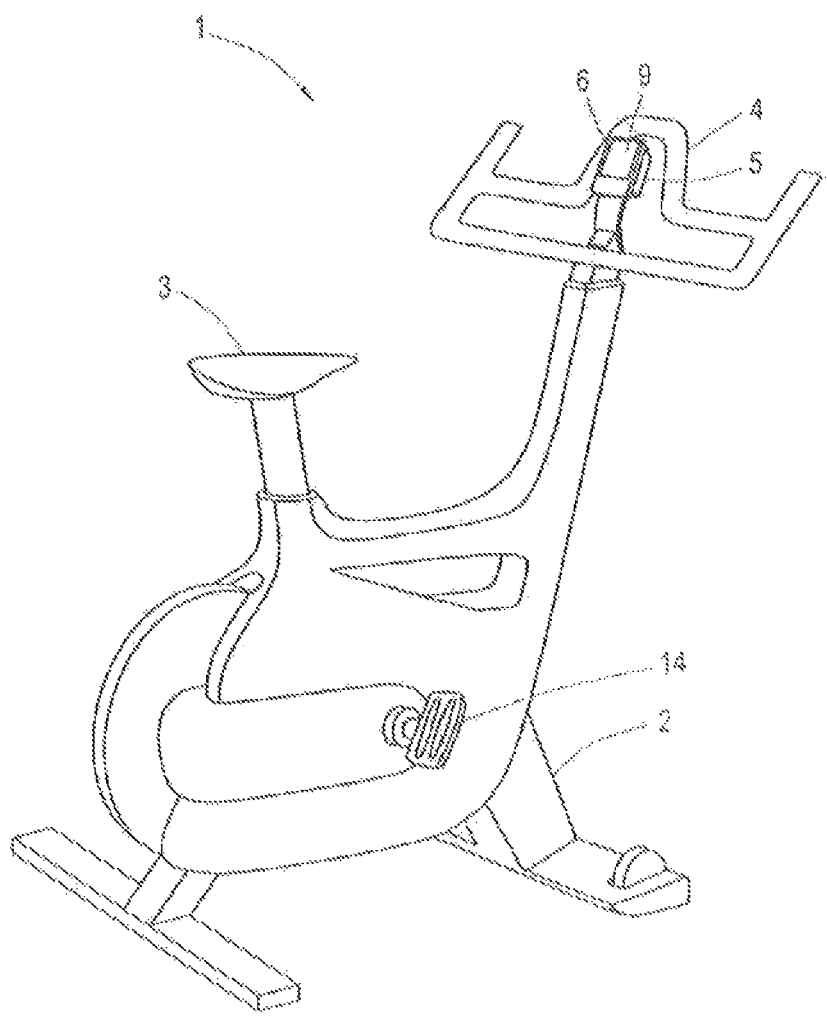
FIG. 1 shows a perspective view of exercise equipment according to the invention, in the form of an exercise bike, with a view of the first display apparatus.

FIG. 1 shows stationary exercise equipment 1 according to the invention, in this case in the form of an exercise bike, comprising a frame 2 with a saddle 3 on which the exerciser takes a seat, and also a handlebar 4 and pedal system 14, by means of which the exerciser drives a movement unit in a known fashion, the latter providing a resistance which said exerciser has to overcome for training purposes.

Provision is furthermore made for a computer apparatus 5 with an associated display apparatus 6. The computer apparatus 5 communicates with one or more sensors which serve to capture different measured values, on the basis of which information to be output is thereupon established. It is conventional for one or more sensors to be located in the region of the bottom bracket of the pedal system 14, i.e. ultimately in the region of the movement unit. These sensors situated there are used to record equipment-related measured values, such as, in particular, the cadence or rotational speed, the power produced while pedaling, and also the level of resistance against pedaling which is provided by the movement unit, for example by setting a specific gear ratio or gear or an incline, etc. All of these, which are established by suitable sensors such as rotational-speed sensor, strain gauge, etc., are provided to the computer apparatus 5 via e.g. cables.

Provision is furthermore made for a chest strap 7, which is worn by the exerciser. On this too there is a sensor 8, which is illustrated in only an exemplary manner in this case and which, as person-related measured value, continuously measures the actual heart rate of the exerciser. This sensor 8 communicates with the computer apparatus, be it via a cable or be it in a wireless fashion, i.e. by radio transmission. It follows from this that, on the computer-apparatus-side, both equipment-related measured values and person-related measured values are available.

In order to obtain a calculation which is as optimal as possible of the training data to be displayed, the computer apparatus furthermore requires the entry of user data by the exerciser himself. This is preferably brought about directly via the display apparatus 6, which, to this end, is designed as a touchscreen and accordingly communicates with the computer apparatus 5. The user data to be entered serve for individualization of the calculation basis for the information to be output in order to enable an efficient and individual training. By way of example, the following user data is entered manually (to the extent that this is known; non-exhaustive list): maximum heart rate, sex, age, weight, training activity, aerobic/anaerobic threshold. FTP-value (the maximum power which a rider can provide in an hour in the case of aerobic/anaerobic metabolism), watt/kg body mass at the anaerobic threshold, training zones (for heart-rate or watt-based training).

The more user data and measured values are available on the computer-apparatus side, the more or more precisely it is possible to optimize the calculation of the information to be output and hence the training control. By way of example, by using the user data and the measured values, the following parameters can be displayed and/or established:

current heart rate
maximum heart rate
current cadence (rotational speed)
maximum cadence (rotational speed)
current power (watt)
maximum power (watt)
training duration current resistance level
maximum resistance level
average heart rate
average cadence (rotational speed)
average power (watt)
average resistance level
distance
speed
percentage of the heart rate in relation to the maximum heart rate
training zones for the heart rate in relation to the maximum heart rate
percentage of the power (watt) in relation to a threshold (index value)
training zones for power (watt) in relation to an index value The aforementioned list of parameters is not exhaustive.

Among these parameters, the percentage of the heart rate in particular and, resulting therefrom, the training zone with respect to the heart rate, is a very important parameter. This is because the given heart rate provides a direct measure for the load on the exerciser.

First, the load is subdivided into five training zones. These training zones emerge as percentage intervals of the maximum heart rate, which in turn emerges from the user-specific parameters (sex; age, weight, training state, etc.). The individual training zones are approximately as follows:

50-60% MHR: health zone
60-70% MHR: burning zone
70-80% MHR: aerobic zone
80-90% MHR: anaerobic zone
90-100% MHR: red zone
MHR=maximum heart rate Each zone is associated with a zone-specific training content. Thus, the health zone is an entry level/rehabilitation load zone, which serves for stabilizing the cardiovascular system and also for regeneration; the subjective load is very light to light. For more practiced sportsmen, there is optimal fat-burning in the fat burning zone; it serves for further strengthening of the cardiovascular system. The subjective load is light to medium. In the aerobic zone there is an increase in endurance and strengthening of the heart and an economization of the cardiovascular and respiratory systems, and also an improvement in the aerobic capacity. Here too there is an increase in the fat-burning rate. The subjective load is medium to tough. In the anaerobic zone there is an upward displacement of the anaerobic threshold, it serves to improve the lactic acid decomposition; the subjective load is tough to very tough. By contrast, the "red zone" is only suitable for professional top-level athletes; here there is a maximum load at the absolute performance limit. The subjective load is extremely tough.

Now, supported by the subjective, person-related data, these training zones are established individually for each person. Since, as described above, the sensor 8 also continuously establishes the actual heart rate during the training, it follows that there is continuous monitoring of the training zone in which the exerciser is currently training. The currently "worked" training zone is now displayed on the first display apparatus 6. To this end, this display apparatus 6 is preferably embodied as a color display 9, on which any colors can be displayed.

It is preferable for each one of the five zones now to be assigned a particular color. By way of example, the health zone is displayed, in a color-coded fashion, in white, the fat-burning zone in blue, the aerobic zone in green, the anaerobic zone in yellow and the "red zone" in red. According to the invention, this color display is preferably brought about such that the whole display area is designed to be in the appropriate, zone-related color, i.e. the background color of the display corresponds to the appropriate zone color. That is to say, the exerciser immediately identifies the zone in which he is training on the basis of the display background color, and so he can monitor himself.

Naturally, appropriate further information is also displayed at the same time on the large-area display; this further information is either measured directly (e.g. current cadence, power, resistance, etc.) or calculated (e.g. average cadence, average power, etc.).

Figure 2:
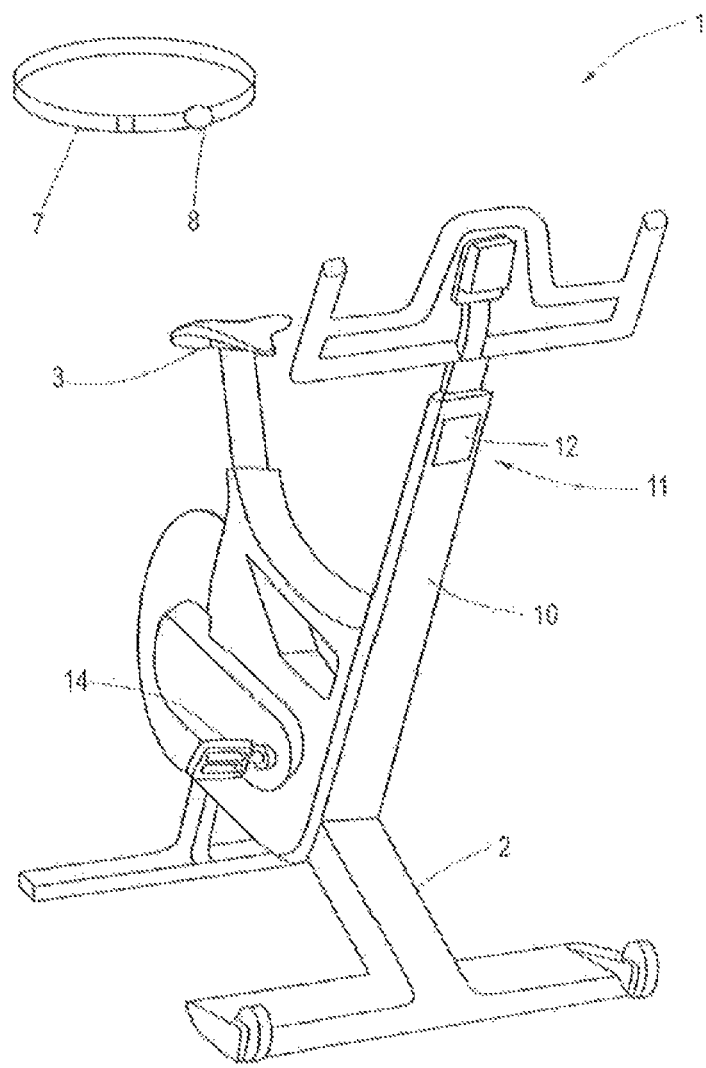
FIG. 2 shows a second perspective view of the exercise equipment from FIG. 1 with a view of the front side and the second display apparatus found there.

As shown in FIG. 2, a second display apparatus 11, which is also in the form of a color display 12 in this case and can optionally be switched on/off independently, is arranged, preferably integrated, on a vertical brace 10 of the frame 2. While the first display apparatus 6, i.e. the color display 9, is directed at the exerciser, the second display apparatus 11 or color display 12 is directed in the opposite direction, i.e. consequently at a trainer who is standing or moving in front of the exercise equipment when a number of participants are training simultaneously within the scope of a group class. This color display 12 likewise communicates with the computer apparatus 5, i.e., in principle, any information, as is also displayed on the first color display 9, can also be displayed thereon.

Thus, information is provided directly to the trainer himself via this set-up, wherein, however, not all the information displayed on the color display 9 is to be displayed on the color display 12. Rather, it is only required at that location for the essential information to be displayed such that the trainer can very quickly note the information and provide optional training commands.

As explained above, one of the essential items of information is the currently "worked" training zone, which ultimately represents the individual performance or load state of the exerciser. This color-coded training zone is now displayed over a large area on the color display 12. The color display 12 shines in the same color that also forms the illuminating background color of the color display 9. That is to say, both color displays 9 and 12 simultaneously shine with the same color such that both the exerciser and the trainer standing on the other side can identify the respectively color-coded training zone by a simple look at the respective display. Since the color display 12 has a relatively large area, it is readily possible for the trainer even to identify the respective color-coded training zone from a significant distance.

The allows the trainer to identify, for example, a change from an aerobic zone, in which the exerciser should actually be "working", to an anaerobic zone, which is disadvantageous to said exerciser from a health perspective, even if said trainer is standing to the side. He can thereupon immediately provide an appropriate command (e.g. reduce the cadence or reduce the resistance) in order thus to control the training in a health-optimized fashion.

Both the first and also, in particular, the second color display 12 can moreover operate in e.g. flashing operation, for example if an aforementioned zone change is present. Such flashing is even more conspicuous, i.e. it is immediately identified by the trainer (and by the exerciser if this is also is the case on the first color display 9), and so countermeasures can be taken.

At this point, reference should be made to the fact that, in place of color-coding, the zones can naturally also be individualized using appropriate, different symbols. Thus, for example, the individual zones can be displayed using the letters A-E (A health zone; E=red zone). These letters can also be displayed over a large area, particularly on the second color display 12 (see FIG. 3A), so that they are identified immediately. If this is a color display, the individual letters can moreover even be displayed in color, i.e. double encoding would then be the case.

Figure 3:
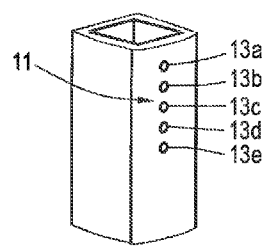
FIG. 3 shows a partial view of exercise equipment for illustrating a further embodiment of the second display apparatus in the form of individual LEDs.
Figure 3A:
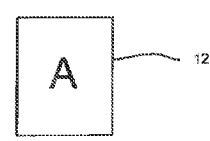
FIG. 3A shows a front view of display apparatus according to an embodiment of the invention.

FIG. 3 finally shows a further embodiment of a second display apparatus 11. The latter is embodied here in the form of a plurality of separate and individually actuatable light sources 13a-13e. The light sources are LEDs, for example. What is important is that the individual light sources have different colors such that, once again, a specific, color-coded associated training zone can be displayed by means of respectively one light source or LED. By way of example, the light source 13a is provided as white-light source for displaying the health zone, the light source 13b emits blue light and is associated with the fat-burning zone, the light source 13c emits green light and is associated with the aerobic zone, the light source 13d emits yellow light and is associated with the anaerobic zone, while the light source 13e emits red light and is associated with the "red zone". Thus, it follows that, firstly, the background color shines on the first color display 9 and also, simultaneously, that the corresponding color-assigned light source 13a-13e shines, depending on which zone is currently being "worked".

In principle, it is naturally also feasible to design the individual light sources 13a-13e such that each light source can emit an arbitrary color, for example by the installation of corresponding LED groups (RGB groups); this means that arbitrary colors can be generated at the respective light source by light mixing. This in turn renders it possible for all light sources to provide emissions of the same color, with it however being possible to set the respective color. Thus, this results in a light band, by means of which the respective training zone is letterized.

The option of a flashing display is once again also provided in this embodiment, for example during a change from one zone to another, i.e. during a change from one color to another.

Figure 4:
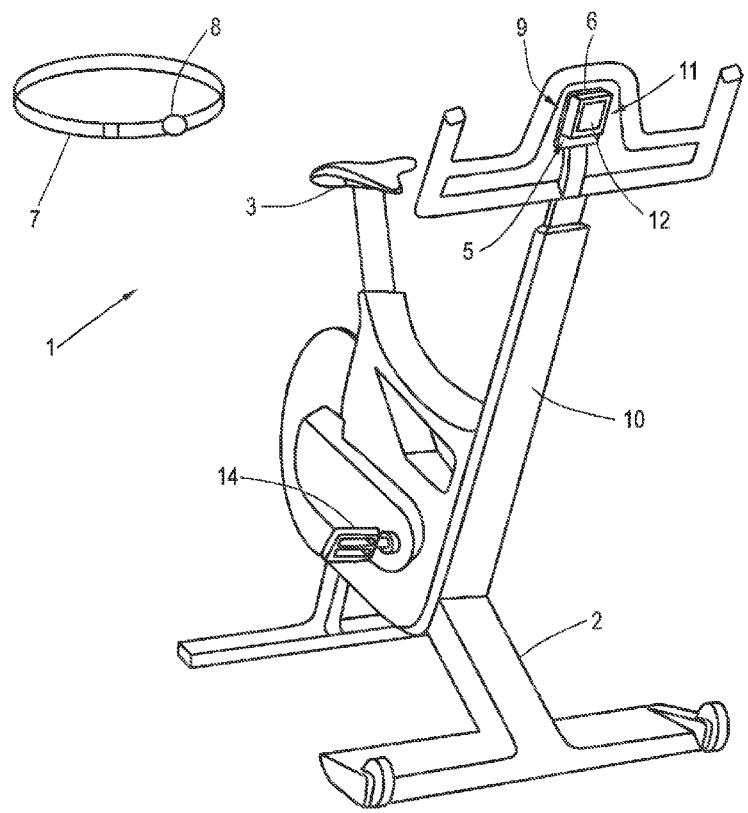
FIG. 4 shows a perspective view corresponding to FIG. 2, wherein the first display apparatus, the second display apparatus and the computer apparatus are provided on or in a common housing.

FIG. 4 finally shows exercise equipment 1 in the form of an exercise bike, as already known from FIGS. 1 and 2. Reference is made to the explanations in this respect. In contrast to the embodiment there, the first display apparatus 6 (preferably again in the form of a color display 9, optionally embodied as a touchscreen), the second display apparatus 11 (preferably likewise in the form of a color display) and the computer apparatus 5 are in this embodiment arranged on or in a common housing which is installed on the handlebar side. Since a computer apparatus usually has a corresponding housing in which the required components are housed, it seems appropriate to attach the two display apparatuses 6 and 11 on this housing, with the one display apparatus once again being directed at the exerciser and the other one being directed to the opposite side. In place of a color display, particularly as a second display apparatus, provision can naturally also be made for individual, different color LEDs in this case. These can also be integrated in the housing and back-illuminate a transparent cove of the housing such that, on the observer side, an appropriately larger-area color display is visible.

The invention claimed is:

1. A stationary exercise equipment for physical training, comprising:
    a frame with a movement unit that is configured to be moved by an exerciser or is itself driven and interacts with the exerciser,
    one or more sensors, assigned to the movement unit or configured to be assigned to the exerciser, for capturing measured values,
    a computer apparatus for establishing one or more items of measurement-value-related information,
    a first display apparatus directed rearward at the exerciser for displaying one or more items of information, and
    a second display apparatus mounted on the frame on a front side of the stationary exercise equipment and directed frontward for outputting at least one item of information to a different person other than the exerciser in front of the stationary exercise equipment,
    wherein an identical color-coded information indicating a current training zone of the exerciser is displayed on the first display apparatus and the second display apparatus simultaneously so that the current training zone is displayed to the exerciser and to the different person, wherein the current training zone is one of a plurality of training zones, each of the training zones corresponding to a different percentage interval of the maximum heart rate of the exerciser or a different percentage interval of power in relation to an index value, and each of the plurality of training zones is assigned a respective zone-specific color as the color-coded information;
    wherein the identical color-coded information is output by a flashing display having a flashing operation on each of the first display apparatus and the second display apparatus, wherein the flashing operation displays change in the current training zone.

2. The stationary exercise equipment according to claim 1, wherein the frame has at least one vertical or at least one horizontal brace, on which the second display apparatus is arranged.

3. The stationary exercise equipment according to claim 2, wherein the second display apparatus is integrated into the vertical or horizontal brace.

4. The stationary exercise equipment according to claim 1, wherein a plurality of identical items of information are adapted to simultaneously be displayed by the first and the second display apparatus.

5. The stationary exercise equipment according to claim 1, wherein the zone-specific color is presented as a display background on the first display apparatus and the second display apparatus.

6. The stationary exercise equipment according to claim 1, wherein the identical color-coded information is displayed on both displays by letters, text or symbols.

7. The stationary exercise equipment according to claim 1, wherein the first display apparatus, the second display apparatus and the computer apparatus are arranged on or in a common housing.

8. The stationary exercise equipment according to claim 1, wherein the color-coded information is presented as zone-specific colored letters.

9. The stationary exercise equipment according to claim 1, wherein each of the training zones corresponds to a different percentage interval of the maximum heart rate of the exerciser.

10. The stationary exercise equipment according to claim 1, wherein each of the training zones corresponds to a different percentage interval of power in Watts in relation to an index value.

11. The stationary exercise equipment according to claim 1, wherein the second display apparatus is switchable on/off independently.

* * * * *